United States Patent [19]
Ogino

[11] Patent Number: 5,422,712
[45] Date of Patent: Jun. 6, 1995

[54] APPARATUS FOR MEASURING FLUORESCENT SPECTRA OF PARTICULES IN A FLOW

[75] Inventor: Shinichi Ogino, Kobe, Japan

[73] Assignee: Toa Medical Electronics Co., Ltd., Kobe, Japan

[21] Appl. No.: 34,376

[22] Filed: Mar. 18, 1993

[30] Foreign Application Priority Data

Apr. 1, 1992 [JP] Japan .................................. 4-108828

[51] Int. Cl.⁶ .......................................... G01N 21/64
[52] U.S. Cl. ..................................... 356/73; 356/318; 356/417; 250/458.1; 250/461.2
[58] Field of Search .................. 356/417, 72, 73, 317, 356/318; 250/458.1, 459.1, 461.1, 461.2

[56] References Cited

U.S. PATENT DOCUMENTS

| | | | |
|---|---|---|---|
| 4,586,820 | 5/1986 | Yokoyama et al. | 356/317 |
| 4,690,561 | 9/1987 | Ito | 356/73 |
| 4,988,619 | 1/1991 | Pinkel | 356/73 |
| 5,123,731 | 6/1992 | Yoshinaga et al. | 356/73 |
| 5,148,031 | 9/1992 | Kamalov et al. | 356/318 |
| 5,159,397 | 10/1992 | Kosaka et al. | 356/73 |
| 5,159,398 | 10/1992 | Maekawa et al. | 356/73 |
| 5,159,642 | 10/1992 | Kosaka | 356/23 |
| 5,185,265 | 2/1993 | Steen et al. | 356/73 |
| 5,260,764 | 11/1993 | Fukuda et al. | 356/318 |
| 5,272,354 | 12/1993 | Kosaka | 356/336 |

FOREIGN PATENT DOCUMENTS 61-178645  8/1986  Japan ................................. 356/318

Primary Examiner—Rolf Hille
Assistant Examiner—Minhloan Tran
Attorney, Agent, or Firm—Jones, Tullar & Cooper, P.C.

[57] ABSTRACT

A sample liquid flow containing particle components such as blood and urine is illuminated with light, and signals from particles are detected, and the particles are thereby analyzed. In this apparatus, using a prism or a diffraction grating, spectra of light signals are obtained, and more specific information regarding the particles is obtained. The fluorescence from the particles is separated by a prism or diffraction grating and classified into wavelength, the intensity of the obtained fluorescence spectra is amplified by an image intensifier, and the intensity is measured for each wavelength by an image sensor.

6 Claims, 10 Drawing Sheets

APPARATUS FOR MEASURING FLUORESCENT SPECTRA OF PARTICLES IN A FLOW

BACKGROUND OF THE INVENTION

The present invention relates to an apparatus for analyzing particles by passing a sample liquid containing particle components such as blood and urine in a sheath flow, and measuring the fluorescent spectra of the particles in the flow. The sample liquid is irradiated with light, signals detected from the particles, and the particles analyzed; and more particularly to an apparatus for analyzing particles capable of obtaining spectra of light signals by using spectroscopic (spectral) means such as prism and diffraction grating, thereby obtaining more specific particle information. The sheath flow is a flow having a suspension of particles the surroundings of which are covered with a laminar sheath liquid in order to align the particles in one row precisely in the middle of the liquid flow to allow passage. As the sheath liquid, usually, a diluent liquid or the like is used.

A fluorescent excitation (excited) light is irradiated to a sample liquid containing particles of dyed cells or the like, and the fluorescence emitted from the particles is detected, and the particles are classified and counted. An example of such an apparatus is a flow cytometer. Also known is an imaging flow cytometer for picking up the particle images.

In such an apparatus, when measuring the fluorescence emitted from the cells, in order to separate the desired fluorescence from other light, wavelength selection means such as an optical filter and a dichroic mirror is needed. Besides, when measuring a plurality of fluorescences differing in wavelength, a corresponding plurality of optical detectors are needed.

The Japanese Laid-open Patent Hei. 2-24535 discloses a flow cytometer capable of calculating the fluorescence intensity distribution of the wavelength of the particles to be detected, by separating the fluorescence from the specimen into consecutive wavelength components by spectroscopic means, and detecting the separated wavelength components by a one-dimensional photoelectric detector.

With an optical filter, however, it is difficult to separate the beams of light that are close in wavelength, although it is possible to separate the beams of light largely apart from each other in wavelength. In addition, the wavelength distribution of the light cannot be measured. That is, it is not possible to know the fluorescence of which wavelength is emitted from which positive of a cell by what quantity. Of course it may be possible by taking the picture of a cell image by a video camera and analyzing the image, but each cell must have a pictured image and the image processed. The apparatus thus becomes complicated.

In the apparatus for analyzing particles disclosed in the Japanese Laid-open Patent Hei. 2-24535, moreover, since the separated fluorescence is weak, it is difficult to detect the fluorescence directly by the detector. By raising (increasing) the lighting (irradiation) intensity of the light for fluorescence excitation, the fluorescence intensity may be enhanced, but the particles to be analyzed may be damaged in this case.

Besides, when using a photoelectric conversion element of the charge accumulation type such as a charge coupled device (CCD), unless the accumulated charge is reset in some way or other, the fluorescence of all the particles passing through the detection region is added up (integrated). Since the particle interval is not constant, it is necessary to detect the passing of a particle, and reset the charge on every occasion.

OBJECT AND SUMMARY OF THE INVENTION

It is hence a primary object of the present invention to provide an apparatus for analyzing particles by measuring the fluorescence spectrum at high precision in every particle even if the fluorescence is feeble.

To achieve this object, in the present invention, the fluorescence from the particles is separated by spectroscopic means such as a prism and a diffraction grating, the intensity of the fluorescence spectrum obtained by the spectroscopic means is amplified by amplifying means such as an image intensifier, and the intensity is measured by the image sensor in each wavelength.

The apparatus for analyzing particles of the present invention is, as shown in FIG. 1 and FIG. 3, an apparatus for detecting particles by forming a sheath flow, wrapping a sample liquid containing particles in a sheath liquid and passing it into a flow cell 16, and irradiating the sample liquid flow 18 with light, comprising:

a light source 10 for irradiating the sample liquid flow 18 with fluorescence excitation (excited) light, spectroscopic (spectro) means 28 for separating the fluorescence emitted in a specific direction from the fluorescence emitted from the particles, and obtaining fluorescence spectra, amplifying means 30 for amplifying the fluorescence spectra obtained in the spectroscopic means 28, an image sensor 34 for detecting each element of amplified fluorescence spectra, and signal processing means 38 for reading out and resetting a signal of the image sensor 34 every time a particle passes.

In this apparatus for analyzing particles, as shown in FIG. 4 and FIG. 5, furthermore, light (photo) detecting means 36 may be provided for detecting scattered light emitted from the particles or transmitted light passing through the particles.

Moreover, as shown in FIG. 6, FIG. 8 and FIG. 9, a second light source 40 for emitting white pulse light to the particles, and image pickup means 52 for picking up white transmitted light images passing through the particles may be also provided.

Also, as shown in FIG. 1, the light detecting means 36 may be disposed to detect forward scattered light and forward fluorescence, and/or as shown in FIG. 4, the light detecting means 36 may be disposed to detect the forward scattered light and backward fluorescence, and/or as shown in FIG. 5, the light detecting means 36 may be disposed to detect the side scattered light and backward fluorescence.

Moreover, as shown in FIG. 6, the fluorescence spectra detecting system and the particle image pickup system may be disposed on a same optical axis, and/or as shown in FIG. 9, the fluorescence spectra detecting system and the particle image pickup system may be disposed orthogonally to each other, and/or as shown in FIG. 8, the first light source irradiation system and the second light source irradiation system may be disposed orthogonally to each other.

Another apparatus for analyzing particles of the present invention is, as shown in FIG. 10, an apparatus for detecting particles by forming a sheath flow by wrapping a sample liquid containing particles in a sheath liquid and passing it into a flow cell 16, and irradiating the sample liquid flow with light, wherein the sample liquid flow is a flat flow 64 broad (wide) in one direction and narrow in another direction, comprising:

a light source 10 for irradiating the sample liquid flat flow 64 with fluorescence excitation (excited) light, spectroscopic means 28 for separating the florescence emitted from the broader side of the sample liquid flat flow out of the fluorescence emitted from the particles and obtaining a fluorescence spectra, amplifying means 30 for amplifying the fluorescence spectra obtained by the spectroscopic means 28, a two-dimensional image sensor 70 for detecting each element of the amplified fluorescence spectra, and signal processing means 72 for reading out and resetting the signal of the two-dimensional image sensor 70 every time a particle passes through.

In the apparatus shown in FIG. 10, furthermore, light detecting means 36 may be provided for detecting the scattered light emitted from the particles in the broader side of the sample liquid flat flow or the transmitted light passing through the particles.

In the apparatus shown in FIG. 10, and in particular shown in FIG. 12, a second light source 40 for emitting white pulse light to the particles, and image pickup means 52 for picking up the white transmitted light passing through the particles may also be provided.

The fluorescence emitted from the particle by irradiation with fluorescence excitation light is separated by the spectroscopic means 28, and a fluorescence spectral image is obtained. This fluorescence spectrum is amplified by amplifying means such as image intensifier 30, and the intensity is measured in each wavelength by the image sensor 34 or 70.

As to the image sensor, when a plurality of lines of one-dimensional image sensor are provided, the fluorescence spectra of a plurality of particles can be measured simultaneously.

On the other hand, the fluorescence excitation light passing through the particles and the scattered light scattered by the particles are detected by the light detecting means 36, and passing of the particles is judged in a signal processor 38. When passing of the particle is over, the signal of the image sensor is read out, and the image sensor is reset.

DETAILED DESCRIPTION OF THE PREFERRED EMBODIMENTS

Embodiment 1

Figure 1:
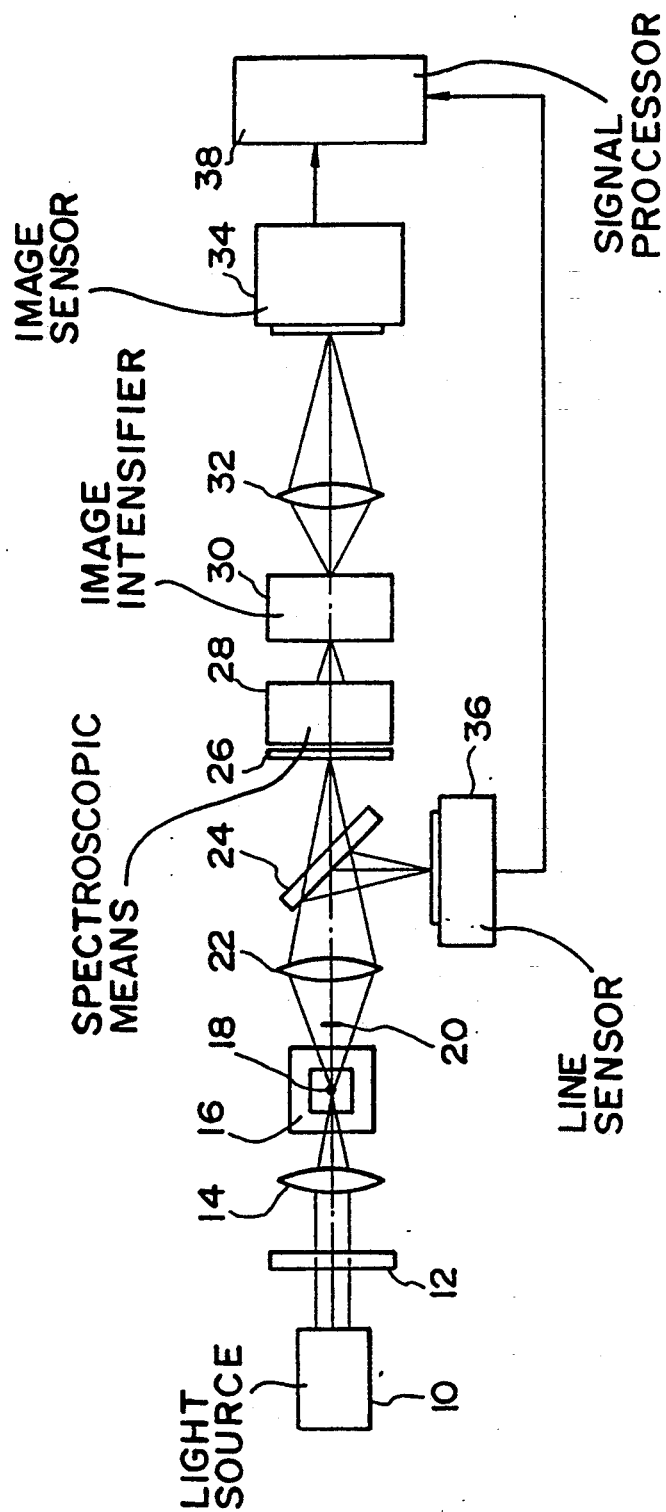
FIG. 1 is a schematic diagram showing an embodiment of an apparatus for analyzing particles of the present invention.

FIG. 1 is a schematic diagram of an apparatus for analyzing particles according to Embodiment 1.

A light source 10 is a fluorescence excitation (excited) light source, which is a laser light source such as an Ar, He-Cd or semiconductor layer, or a light source of continuous emission type such as a Xe lamp. When the light source with a continuous spectrum, such as a Xe lamp is used, a desired excitation (excited) wavelength can be selected by using a wavelength selection filter 12. When the laser light source is used, the filter 12 is unnecessary.

A condensing lens 14 is a lens for focusing the light from the fluorescence excitation light source 10 into a sample liquid flow 18 flowing in the center of a flow cell 16, and the spot size when concentrated is desired to be about $10 \times 200$ μm.

The flow cell 16 is made of transparent material, such as glass or plastic, and comprises a lead-in passage narrowed gradually, a narrow measuring passage connected to the lead-in passage, a sheath liquid feeding port provided in the lead-in passage, and a discharge port provided downstream of the measuring passage.

When the particles to be analyzed pass through the illumination region of the fluorescence excitation light, scattered light (forward scattered light) and fluorescence (forward fluorescence) are obtained. This light is collected by a receiving lens 22. Numeral 20 is a shield plate for shielding the direct light from the light source 10.

The scattered light is reflected by a dichroic mirror 24, and enters light detecting means, such as a CCD line sensor 36. The signal from the line sensor 36 is fed into a signal processor 38, where passage of the particle is detected. At the same time, the size and number of passing particles are detected. When sensing a particle by the transmitted light, the shield plate must be removed.

Figure 2:
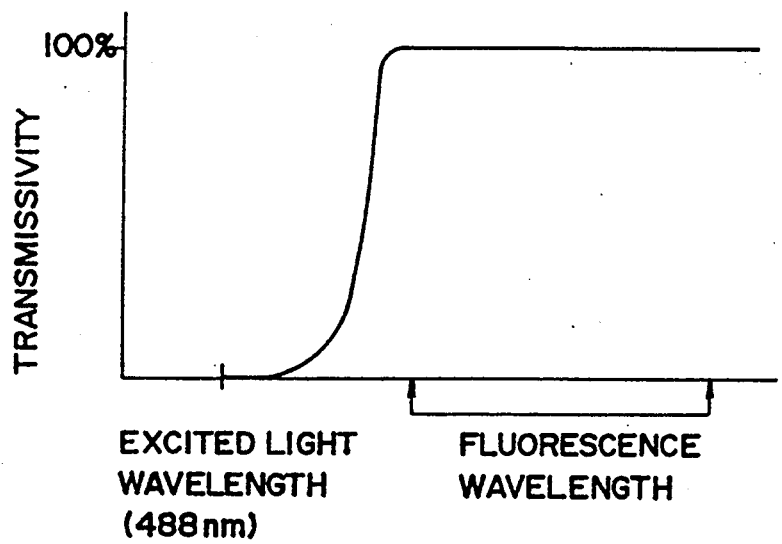
FIG. 2 is a characteristic diagram of the dichroic mirror in FIG. 1.

On the other hand, the fluorescence passes through the dichroic mirror 24, passes through a slit 26 and enters spectroscopic means 28. FIG. 2 shows the characteristic diagram of the dichroic mirror 24.

Figure 3:
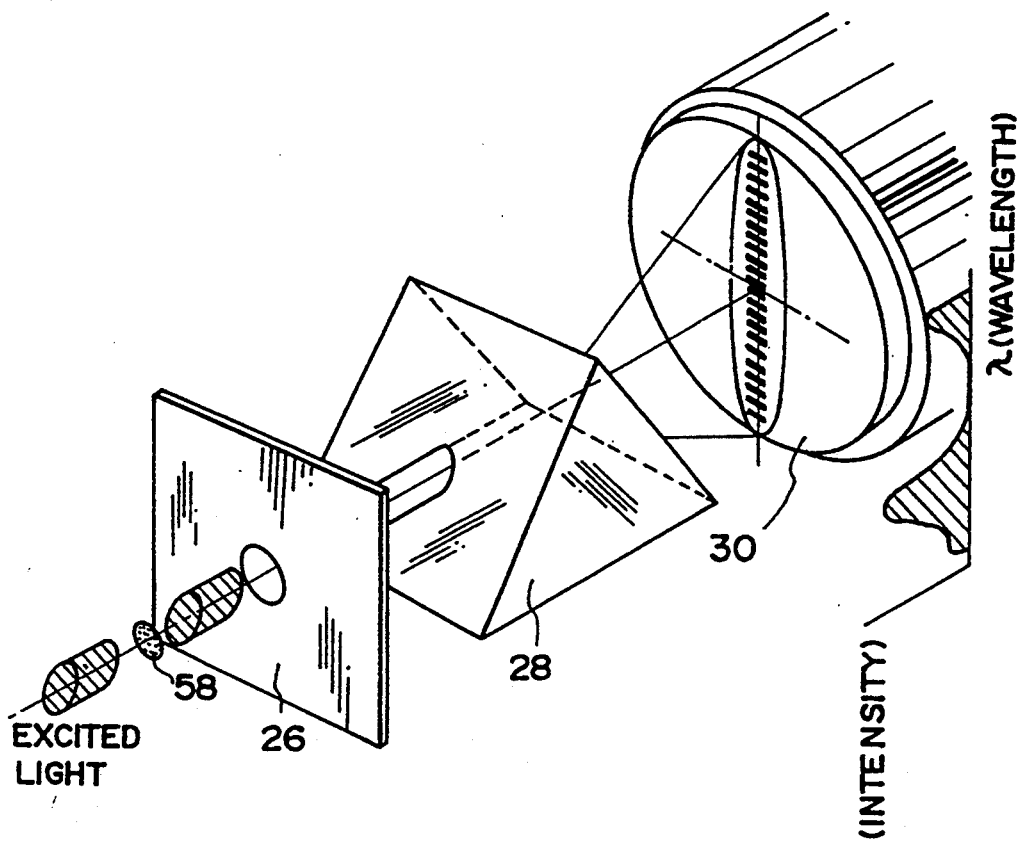
FIG. 3 is a perspective explanatory diagram for explaining the detail concerning the spectroscopic means in FIG. 1.

The spectroscopic means 28 converts the fluorescence emitted from the cell into a spectrum. For example, by using a polychromator, a prism and a lattice (grating), a fluorescence spectral image as shown in FIG. 3 is obtained on the incident plane of the amplifying means, such as an image intensifier 30. Numeral 58 denotes a particle.

The image intensifier 30 is a photoelectron multiplier, and is used for amplifying the fluorescence spectral image separated by the spectroscopic means 28. The fluorescence spectral image entering the incident plane (photoelectric plane) of the image intensifier 30 is amplified, and sent out to an output plane (fluorescence plane) of the image intensifier 30. Furthermore, the fluorescence spectral image sent out to the image intensifier 30 is focused (formed) on a light receiving element (image sensor) 34 by a relay lens 32 or an optical fiber.

By using a CCD line sensor or a photo diode array as the light receiving element (image sensor) 34, the fluorescence intensity for each wavelength is measured. For example, using a CCD line sensor with 256 pixels of 13 $\mu$m each, measuring the wavelength in the region from 400 to 656 nm, and properly setting the focal length of the spectroscopic means 28, the fluorescence intensity can be measured at a resolution of 1 nm per pixel.

When a CCD line sensor is used as a light receiving element (image sensor) 34, since it is of the charge accumulation type which is different from the photo diode array, the accumulated charge must be reset in some way or other (otherwise the fluorescence intensity of all passing particles is counted (added) up). Accordingly, by making use of the signal from the line sensor 36 as the light detector, the accumulated charge is read out after passage of every particle, and the charge is reset. In addition, by processing the signal from the line sensor 36, it is judged whether the particle is the object of measurement or not, and in the case where the particle is not to be measured, the fluorescence spectral signal is reset from the CCD line sensor 34 before delivering a signal to the signal processor 38, so that only necessary data is taken in.

The obtained signal is processed by the signal processor 38, and the spectral data may be obtained for every passing particle.

In the apparatus of the present invention, the excitation (excited) light and fluorescence light in the light receiving element 34 differ in wavelength, and therefore the position of a pixel (picture element) for obtaining each signal varies. Hence, a filter for removing excitation light is not needed.

Besides, for limiting the detecting region in the flow cell 16, a circular or rectangular slit 26 must be installed. Since the size of the slit 26 is determined by the imaging magnification of the receiving lens 22, the size of the slit 26 may be 0.2 mm in diameter in the case where, for example, the detecting region in the flow cell is 20 $\mu$m in diameter and the imaging magnification of the receiving lens 22 is 10 times.

Thus is realized a flow cytometer capable of acquiring fluorescence in two or more types (kinds) of wavelengths by using one detecting system.

Embodiment 2

The apparatus in FIG. 1 is designed to detect the forward scattered light and forward fluorescence by the light (fluorescence excitation light) from the light source 10, but other embodiments can also be realized.

Figure 4:
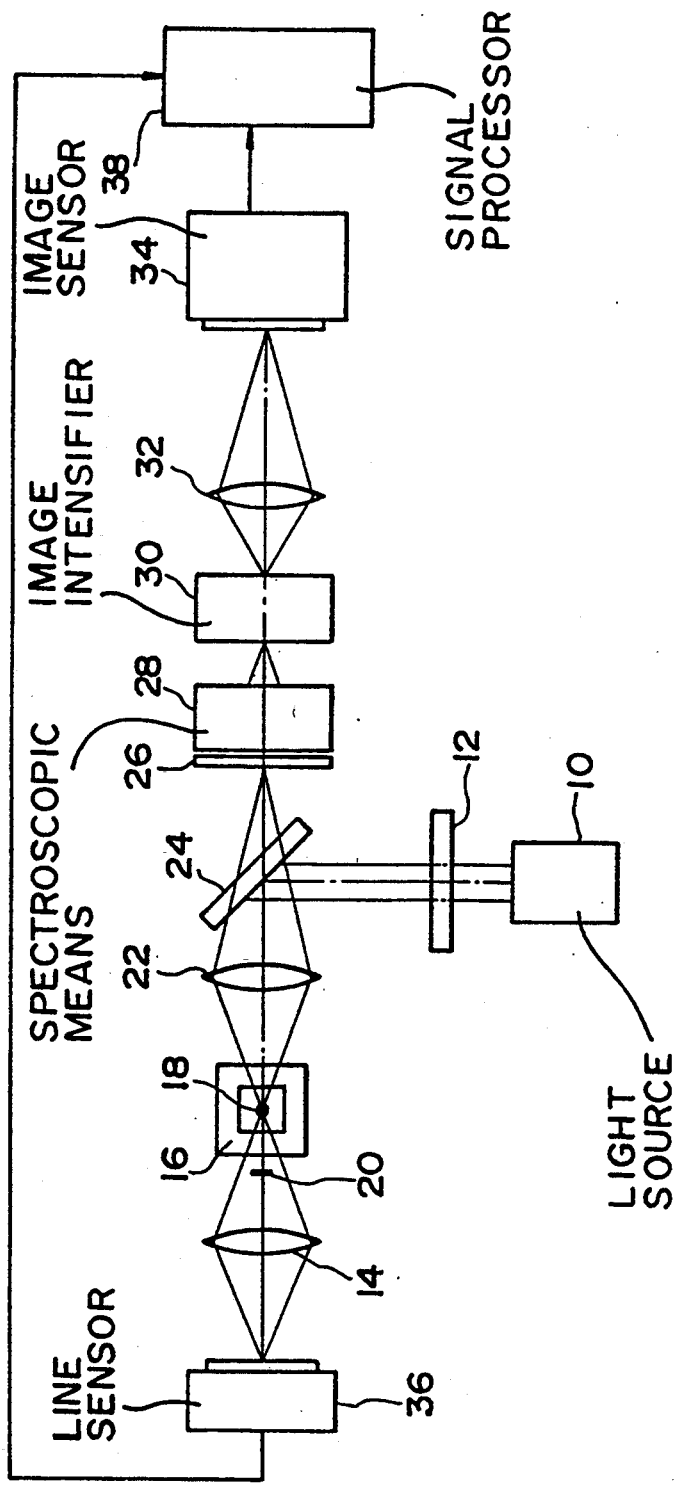
FIG. 4 is a schematic diagram showing another embodiment of the present invention.

For example, FIG. 4 is a schematic diagram of an apparatus for analyzing particles according to an Embodiment 2.

The apparatus in FIG. 4 is different from the apparatus in FIG. 1 in the configuration (arrangement) of the illumination system by the light source 10 (illumination system of fluorescence excitation light) and the scattered light detection system by the light (photo) detecting means 36, because the apparatus in FIG. 4 is intended to detect the forward scattered light and backward fluorescence.

By the arrangement of the irradiation system and the mirror 24, the excitation light from the light source 10 does not enter directly into the fluorescence detecting system, so that a high precision fluorescence measurement is realized.

Embodiment 3

Figure 5:
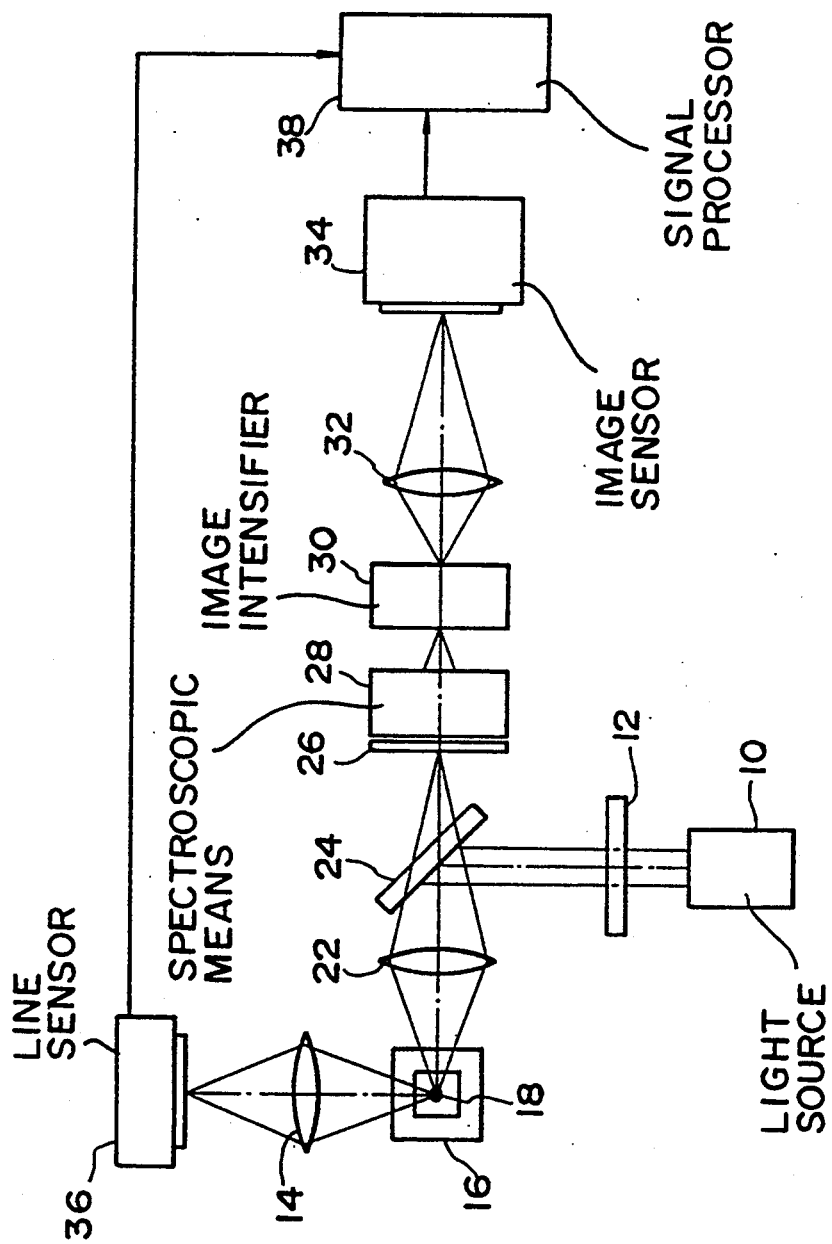
FIG. 5 is a schematic diagram showing still another embodiment of the present invention.

FIG. 5 is a schematic diagram of an apparatus for analyzing particles according to an Embodiment 3.

The apparatus in FIG. 5 is different from the apparatus in FIG. 4 in the arrangement of the scattered light detecting system by the light detecting means 36, because the apparatus in FIG. 5 is intended to detect the side scattered light and backward fluorescence. The shielding plate 20 for detecting the side scattered light is not needed.

In this case, too, the same effects as in the apparatus in FIG. 4 may be obtained. In addition, since the side scattered light is detected, a signal reflecting (influencing) the difference in the internal structure of the particles may be obtained.

Embodiment 4

Figure 6:
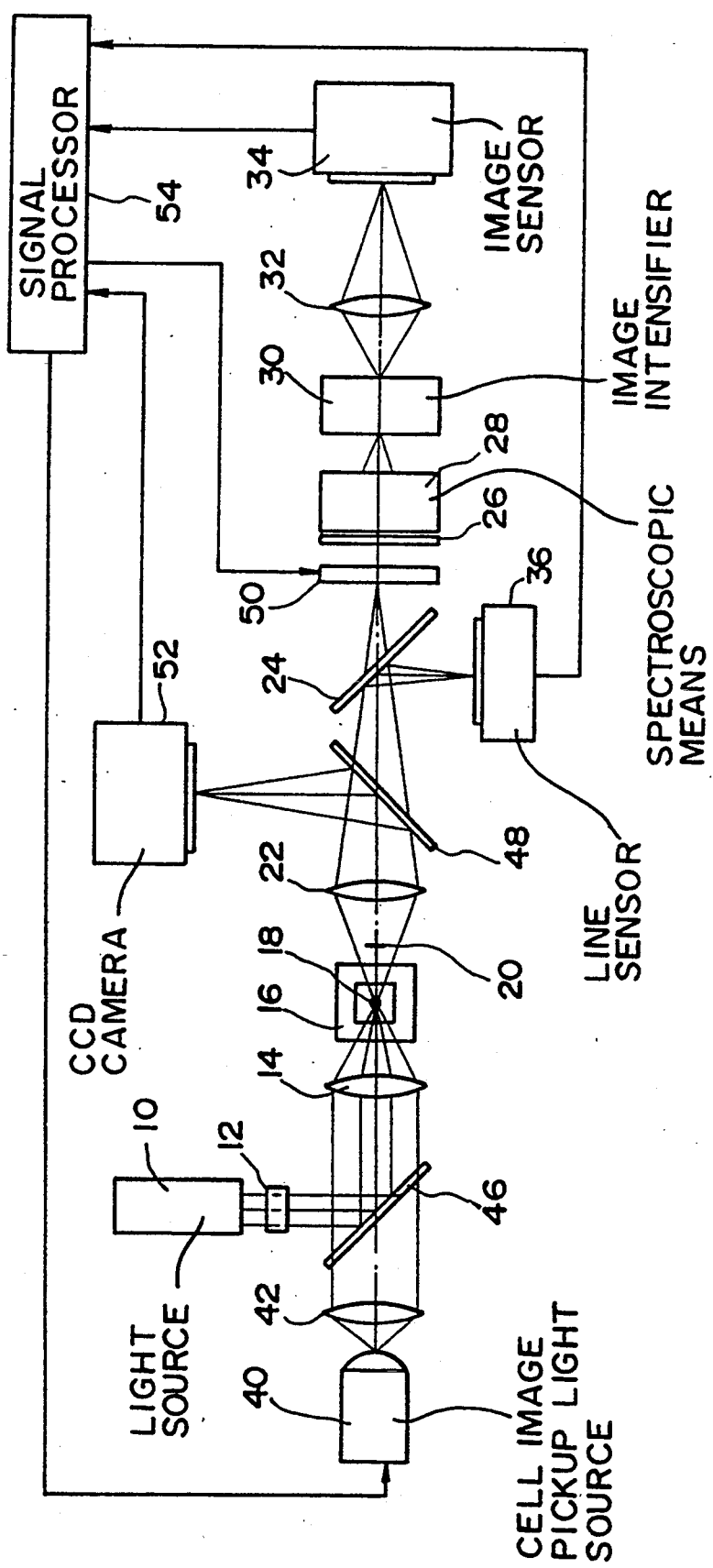
FIG. 6 is a schematic diagram showing a different embodiment of the present invention.

FIG. 6 is a schematic diagram of an apparatus for analyzing particles according to an Embodiment 4.

This embodiment shows a arrangement of an apparatus for picking up the white light images of cells emitting fluorescence at a specific wavelength by utilizing the signal obtained in the apparatus of Embodiment 1. As the light source, in addition to the fluorescence excitation light source 10, a pulse emission type light source in the visible light region (for example, a Xe flash lamp) is used as a cell image pickup light source 40. The irradiation light from the light source 40 is transformed into parallel light in a collimator lens 42, and enters a half-mirror 46.

The half-mirror 46 is used for matching the irradiation regions of the excitation light source 10 and pickup light source 40, and the ratio of transmitted light and reflected light is determined freely by the quantity of light required in the fluorescence receiving system and cell pickup system, but it is desired to heighten the transmissivity of the light from the excitation light source 10 by setting the transmissivity at 90% and the reflectivity at 10% in order to intensify the fluorescence intensity.

A half-mirror 48 is designed to pass the fluorescence obtained from the cell and reflect the cell pickup light, and the ratio of the reflected light and transmitted light can be determined according to the quantity of light required in each system, as is the case with the half-mirror 46.

An electronic shutter 50 is used to prevent excessive light from entering the image intensifier 30 when the cell image pickup light source 40 emits light. Instead of this electronic shutter, an image intensifier possessing a gate function may be used.

Figure 7:
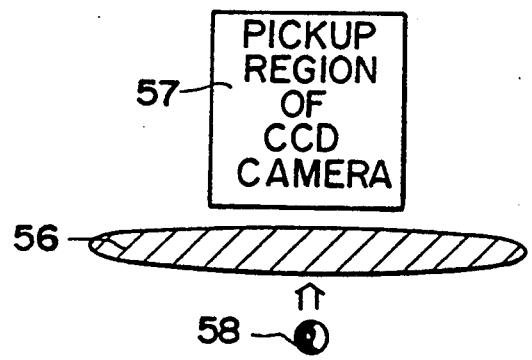
FIG. 7 is an explanatory diagram showing an irradiation region of light source for excitation and an image pickup region of a CCD camera in the flow cell unit in FIG. 6.

The image pickup means, for example, a CCD camera 52 is intended to pick up the white light image of the cell. However, if the pickup region of the CCD camera and the irradiation region of the excitation light are overlapped, the excitation light always enters the CCD camera, and the CCD element is saturated in luminance (brightness), and therefore, as shown in FIG. 7, the irradiation region 56 of the excitation light source 10 and the pickup region 57 of the CCD camera 52 must deviate. Numeral 58 denotes a particle. As the excitation light source 10, if a light source such as a He-Cd laser for emitting the light in the wavelength outside the visible region or at the end of visible region is used, no effect is given to color imaging of the cell image.

The signal processor 54 processes the signal from the light receiving element (image sensor) 34 and judges if the cell in the process of passing the pickup region is the cell to be measured or not, and if judged to be the target cell, a trigger pulse is generated to emit the white image pickup light source 40, while the obtained signal is analyzed.

The measuring procedure is explained below.

The fluorescence excitation light source 10 always illuminates the particle passing region of the flow cell 16, and monitors passing of cells. When a cell dyed in a fluorescent dye passes, the fluorescence emitted from the cell and the passing excitation light are condensed by the receiving lens 22, and pass through the half-mirror 48. The excitation light components are removed by the dichroic mirror 24, and the remaining light passes through the circular slit 26, and enters the spectroscopic means 28. The fluorescence light entering the spectroscopic means 28 is separated into spectra, passes through the electronic shutter 50, and a spectral image as shown in FIG. 3 is focused on the image intensifier 30. This spectral image is amplified by the image intensifier 30, and is sent out to the fluorescent plane of the image intensifier 30. The spectral image produced on the fluorescent plane of the image intensifier 30 is focused (formed on the light receiving element 34 by the relay lens 32. At this time, instead of the relay lens 32, the image may also be focused (formed) on the light receiving element 34 by using an optical fiber.

A similar effect is obtained when the electronic shutter 50 is disposed behind (downstream of) the spectroscopic means 28. Moreover, without using the electronic shutter 50, the same effect may be obtained by using an image intensifier with a gate function.

Afterwards, the detected signal is analyzed by the signal processor 54. When the particle is double-dyed in FITC (fluorescein isothiocyanate) and phycoerythrin, the particle to be measured is dyed in FITC or phycoerythrin or in both, and hence the fluorescence wavelength emitted from the particle is either 530 nm or 570 nm, or both. Accordingly, when either one of the fluorescence intensity at 530 nm and 570 nm is more than a specific value or both are more than specific values, the white light image pickup light source 40 is emitted. Furthermore, the pictured particle images are classified and stored by the fluorescence wavelength (in three types, that is, 530 nm, 570 nm, and both). Or, comparing the measured fluorescence wavelength pattern with a preset fluorescence wavelength pattern, if the wavelength patterns are matched, the white light image pickup light source 40 is emitted.

To pick up a still image of a cell, the emission time of the white light image pickup light source 40 must be a sufficiently short time, otherwise the still image of the cell is not obtained. This emission time is determined by the velocity of the cell passing through the pickup region, and for example, if the cell passing velocity is 1 m/sec, the emission time must be 1 sec or less.

At the same time, the electronic shutter 50 is operated, so that strobe light may not enter the image intensifier 30.

The light emitted from the white light image pickup light source 40 is reflected by the half-mirror 46, and is irradiated into the cell in the flow cell 16. As a result, the light passing through the cell is focused by the receiving lens 22, is reflected by the half-mirror 48, and is focused (formed) on the CCD camera 52.

In this way, the white light image of the cell emitting fluorescence in a specific wavelength is acquired.

Embodiment 5

In the apparatus shown in FIG. 6, the irradiation system of the fluorescence excitation light by the light source 10, and the irradiation system of pulse light for image pickup by the light source 40 are disposed on the same optical axis, and the detection systems of scattered light, fluorescence, and particle passing light image are disposed on the same optical axis so as to detect the forward scattered light, forward fluorescence and transmitted light image. Other embodiments may also be realized.

Figure 8:
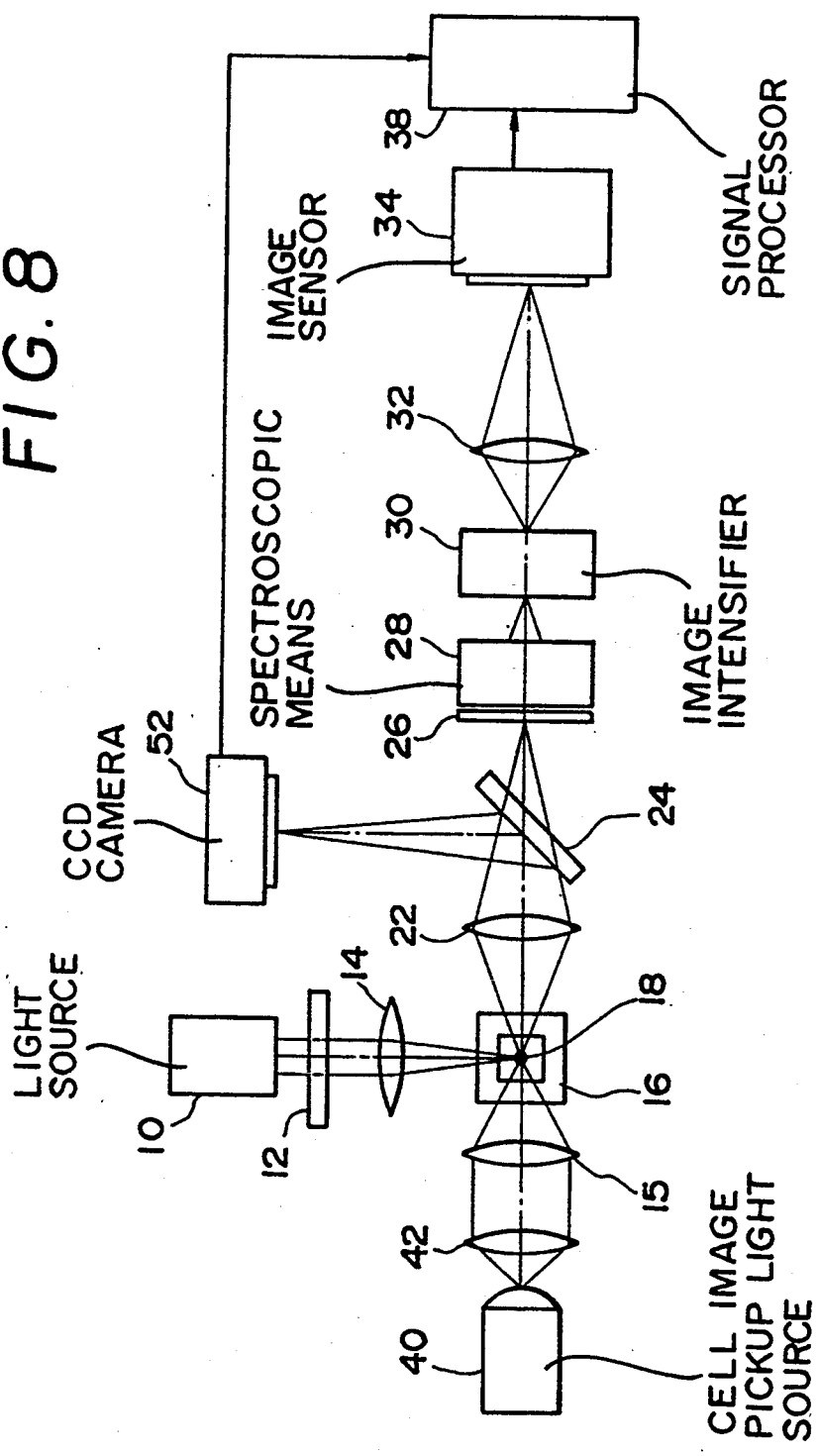
FIG. 8 is a schematic diagram showing another different embodiment of the present invention.

For example, FIG. 8 is a schematic diagram of an apparatus for analyzing particles according to an Embodiment 5.

The apparatus in FIG. 8 is different from the apparatus in FIG. 6 in the arrangement of the irradiation system of the fluorescence excitation light by the light source 10, and is intended to detect the side scattered light by the light source 10, side fluorescence by the light source 10, and transmitted light image by the light source 40. The shield plate 20 for detecting side scattered light is not needed.

Moreover, in the arrangement of the apparatus in FIG. 6, when both the light of the light source 10 and the light of the light source 40 are visible, a half-mirror or dichroic mirror for reflecting the light from the light source 10 must be used as the mirror 46, and therefore the light from each light source cannot be led efficiently into the flow cell 16. However, in the arrangement of the apparatus in FIG. 8, since mirror 46 is not used, it is advantageous because the light from the light source 10 and the light from the light source 40 can be directly and efficiently irradiated to the flow cell 16.

Embodiment 6

Figure 9:
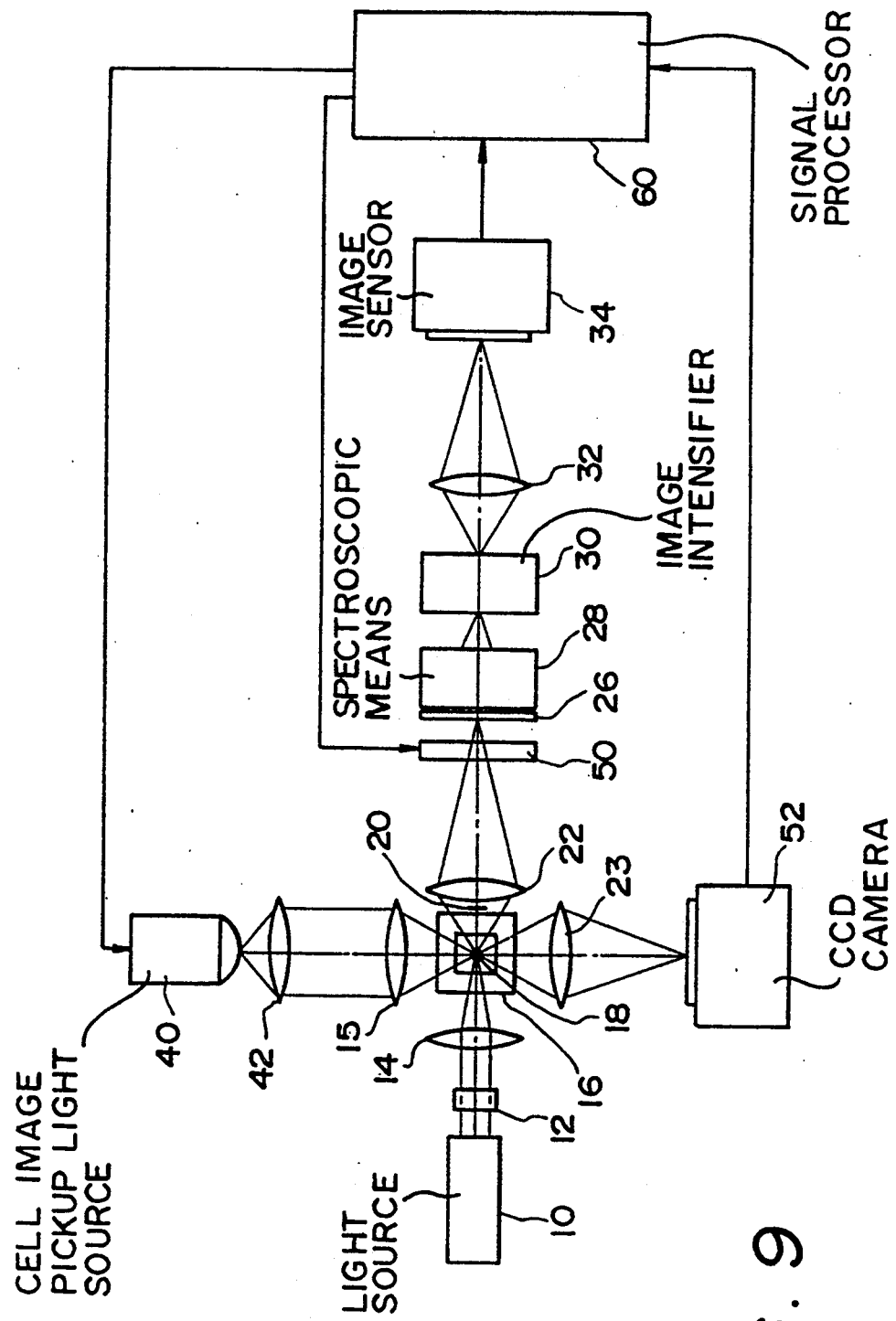
FIG. 9 is a schematic diagram showing still another embodiment of the present invention.

FIG. 9 is a schematic diagram of an apparatus for analyzing particles according to an Embodiment 6.

The apparatus inn FIG. 9 is different from the apparatus in FIG. 6 in the arrangement of the irradiation system of the pulse light for the particle pickup by the light source 40 and the pickup system of the particle transmitted light image. The apparatus in FIG. 9 is intended to detect the forward scattered light by the light source 10, forward fluorescence by the light source 10, and the transmitted light image by the light source 40.

In this embodiment, in the apparatus for analyzing particles according to Embodiment 4, the system for picking up a white light image is disposed at a position orthogonal to the optical system for the detection of fluorescence.

In this arrangement, since it is not necessary to use the half-mirrors 46, 48 in FIG. 6, advantageously, the quantity of light of the light sources 10, 40 can be utilized efficiently. Numeral 15 is a condenser, 23 is a receiving lens, and 60 is a signal processor.

Embodiment 7

Figure 10:
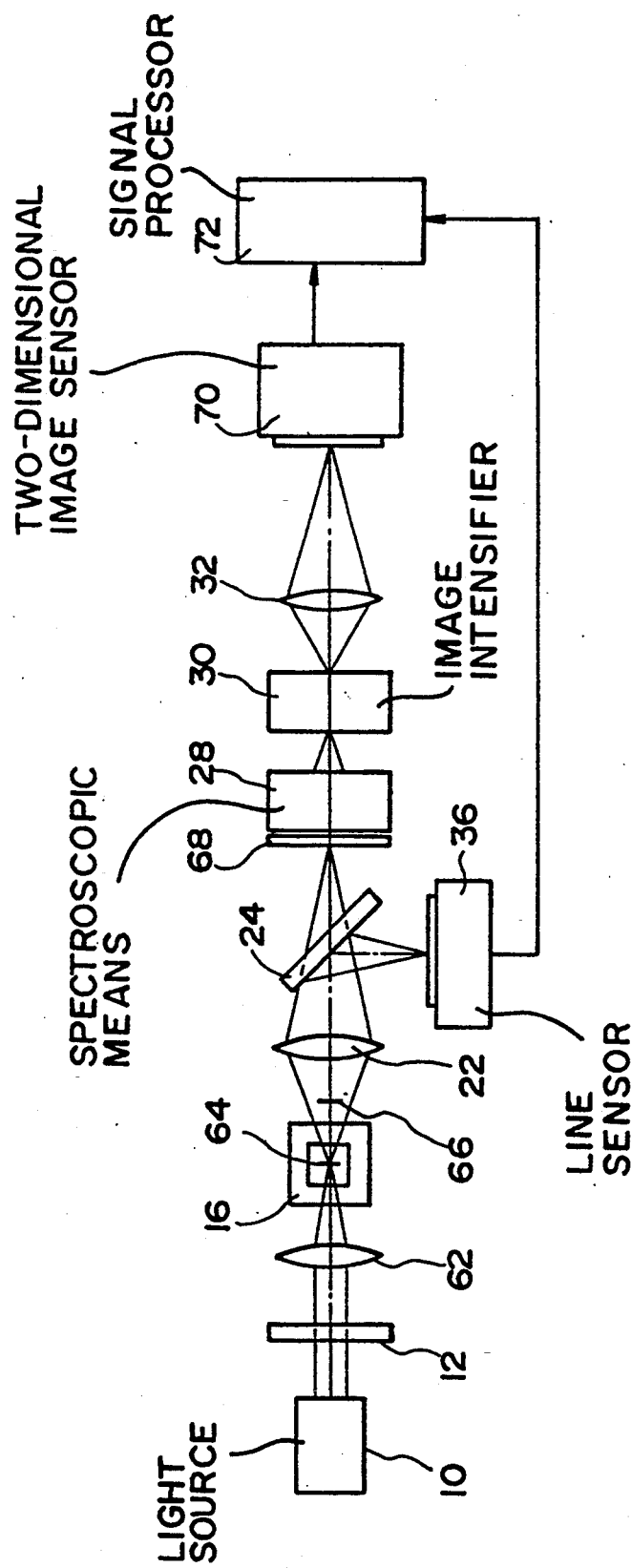
FIG. 10 is a schematic diagram showing a further embodiment of the present invention.

FIG. 10 is a schematic diagram of an apparatus for analyzing particles according to an Embodiment 7.

The basic arrangement of this embodiment is the same as in Embodiment 1. The features of this embodiment lie in the following points: 1. the sample liquid flow is a flat flow 64, instead of a circular flow, 2. the light receiving element for detecting the fluorescent spectral image is a two-dimensional image sensor 70, instead of a one-dimensional image sensor, and 3. the slit is a rectangular slit 68 broad (wide) in the lateral direction, instead of the circular direction.

Figure 11:
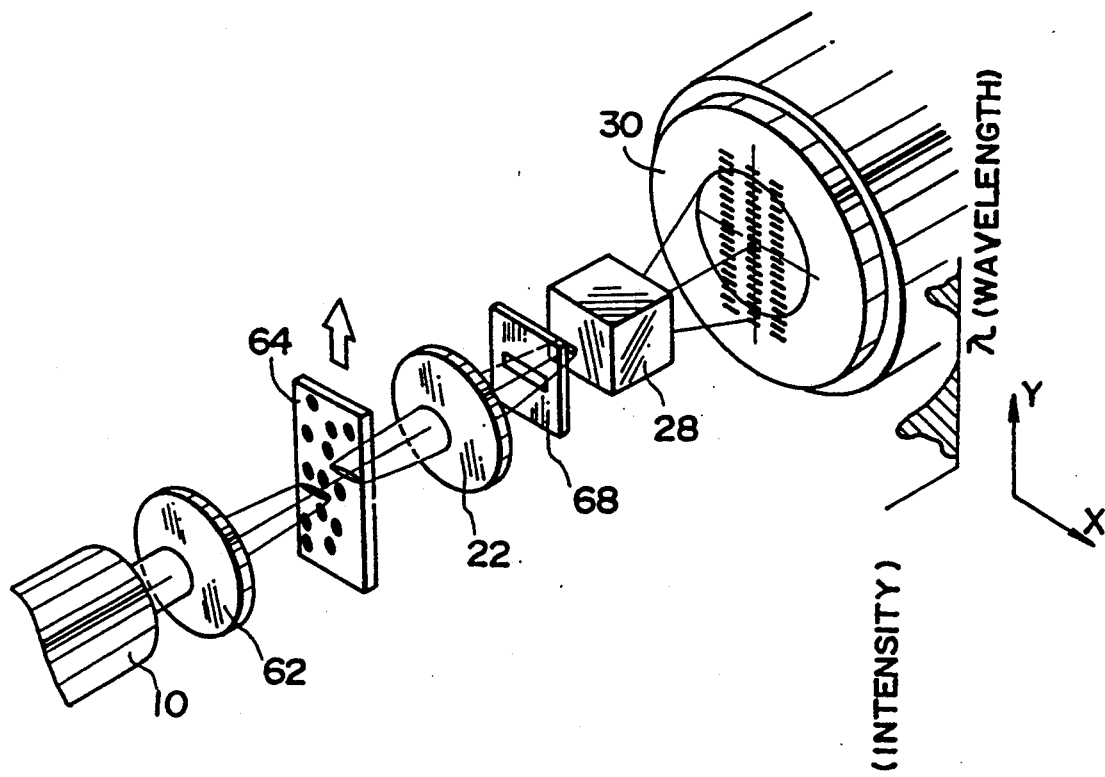
FIG. 11 is a perspective explanatory diagram for explaining the detail concerning the spectroscopic means in FIG. 10.

FIG. 11 is a magnified view of the essential parts in FIG. 10. Since the sample liquid flow 64 is a flat flow, the number of particles to be analyzed can be increased. Besides, using a two-dimensional image sensor 70, a spectral distribution diagram for each point in the X- direction may be obtained. Besides, in order to obtain a flat sample liquid flow 64 in the flow cell 16, the lead-in passage of the flow cell 16 is gradually narrowed in width only in one direction of the passage.

For example, supposing the measuring region in the flow cell 16 to be 20×150 μm and the imaging magnification of receiving lens 22 to be 40 times, when the slit 68 before (upstream of) the spectroscopic means 28 is 6×0.8 mm, the size of one pixel is 40 μm as the light receiving element (two-dimensional image sensor) 70, and the CCD area sensor has 150×250 pixels (150 pixels in the X-direction, 250 pixels in the Y-direction), the fluorescent spectrum from the cell can be measured in the entire measuring region, and the wavelength resolution of 1 nm per 1 pixel of CCD can be attained.

Herein, by processing the signal obtained from the light receiving element 70 by the signal processor 72, the wavelength of the fluorescence emitted simultaneously from a plurality of cells can be measured.

Besides, when the wavelength of the fluorescence emitted from the cells is limited in a specific wavelength region, for example, when using FITC (fluorescein isothiocyanate), phycoerythrin, and propidium iodine as fluorescent dyes, by placing the line type CCD sensor or photo diode array at the Y-axis position corresponding to the wavelengths of 530 nm, 570 nm, and 610 nm, only the intended spectral component can be measured. Numeral 62 is a condenser and 66 is a shield plate.

Embodiment 8

Figure 12:
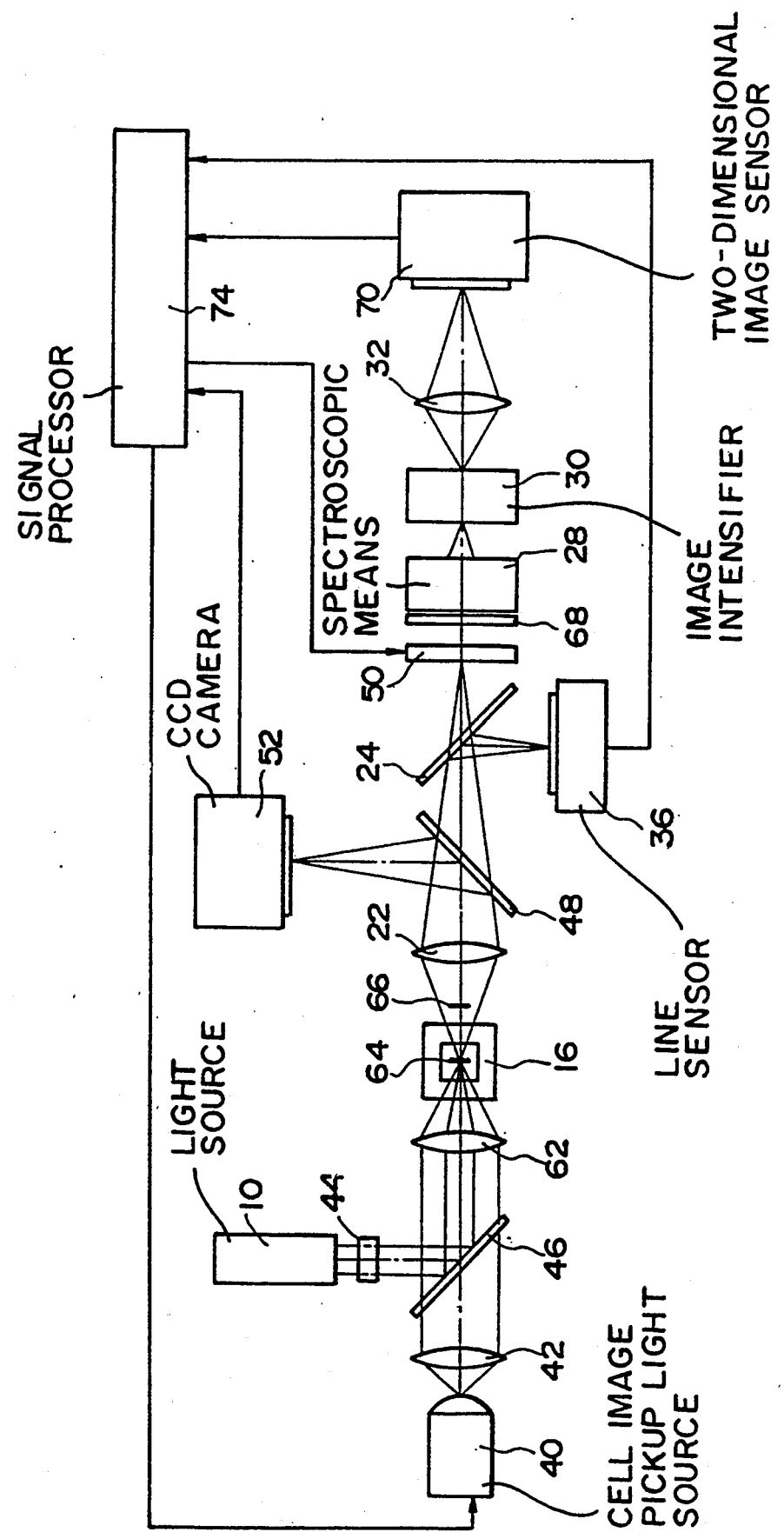
FIG. 12 is a schematic diagram showing another different embodiment of the present invention.

FIG. 12 is a schematic diagram of an apparatus for analyzing particles according to an Embodiment 8.

In this embodiment, the system for white light image pickup is added to the apparatus of Embodiment 7 shown in FIG. 10. In this arrangement, the signal obtained from the detector (two-dimensional image sensor) 70 is analyzed by the signal processor 74, and when a cell emitting fluorescence coinciding with predetermined conditions passes (for example, when double-dyed in fluorescein isothiocyanate and phycoeryrhin, when either 530 nm or 570 nm fluorescence intensity is more than a specific value, or when both are more than specific values), the white light image pickup light source 40 is emitted to form a cell image in the CCD camera 52. Numeral 44 is a wavelength selection filter.

Meanwhile, in the embodiment in which the sample liquid flow is a flat flow, it may be possible to execute by varying the arrangement of the optical system.

Being thus constructed, the present invention brings about the following effects.

(1) The fluorescence from the spectroscopic means such as a prism and a diffraction grating is separated in each wavelength, amplified by an image intensifier, and the intensity measured by an image sensor in each wavelength, and therefore a plurality of fluorescence intensities can be measured simultaneously for individual particles at high precision. Besides, a fluorescent spectral image can be obtained.

(2) The light is separated by spectroscopic means, instead of a wavelength selection filter, so that it is possible to achieve clear separate if the wavelengths are close to each other.

(3) When the sample liquid flow is a flat flow, and a two-dimensional image sensor is used as an image sensor, the florescent spectra of a plurality of particles can be measured at the same time.

Having described preferred embodiments of the present invention with reference to the accompanying drawings, it is to be understood that the present invention is not limited to those precise embodiments, and that various changes and modifications may be effected therein by one skilled in the art without departing from the scope or the spirit of the present invention as defined in the appended claims.

What is claimed is:

1. An apparatus for measuring fluorescent spectra of particles in a flow, being an apparatus for detecting particles by forming a sheath flow by wrapping a sample liquid containing particles in a sheath liquid and passing the sheath flow through a flow cell, and illuminating the sample liquid flow with light, wherein the sample liquid flow is a flat flow broad in one direction and narrow in another direction, the apparatus comprising:

a light source for illuminating the sample liquid flat flow with fluorescence excitation light, spectroscopic means for separating the fluorescence emitted from the broader side of the sample liquid flat flow out of the fluorescence emitted from the particles and obtaining fluorescence spectra, amplifying means for amplifying the fluorescence spectra obtained by the spectroscopic means, a two-dimensional image sensor for detecting each element of the amplified fluorescence spectra, and signal processing means for reading out and resetting a signal of the two-dimensional image sensor every time a particle passes through.

2. The apparatus according to claim 1, wherein, light detecting means is provided for detecting the scattered light emitted from the particles in the broader side of the sample liquid flat flow.

3. The apparatus according to claim 2, wherein, a second light source for emitting white pulse light to the particles, and image pickup means for picking up the white transmitted light passing through the particles are also provided.

4. The apparatus according to claim 1, wherein, a second light source for emitting white pulse light to the particles, and image pickup means for picking up the white transmitted light passing through the particles are also provided.

5. The apparatus according to claim 1, wherein, light detection means is provided for detecting the transmitted light passing through the particles.

6. The apparatus according to claim 5, wherein, a second light source for emitting white pulse light to the particles, and image pickup means for picking up the white transmitted light passing through the particles are also provided.

* * * * *